(12) United States Patent
Adey et al.

(10) Patent No.: US 8,764,985 B2
(45) Date of Patent: Jul. 1, 2014

(54) BASAL SCREEN FOR ENHANCING ALGAL BIOMASS GROWTH

(75) Inventors: Walter H. Adey, Reedsville, VA (US); Erik Thane Adey, Clear, AK (US); Robinson Bazurto, Vero Beach, FL (US)

(73) Assignee: HydroMentia, Inc., Ocala, FL (US)

( * ) Notice: Subject to any disclaimer, the term of this patent is extended or adjusted under 35 U.S.C. 154(b) by 737 days.

(21) Appl. No.: 12/892,849

(22) Filed: Sep. 28, 2010

(65) Prior Publication Data

US 2011/0073542 A1    Mar. 31, 2011

Related U.S. Application Data

(60) Provisional application No. 61/246,477, filed on Sep. 28, 2009.

(51) Int. Cl.
*C02F 3/32*    (2006.01)

(52) U.S. Cl.
USPC .............................. 210/602; 47/1.4

(58) Field of Classification Search
USPC ............................ 210/602; 47/1.4
See application file for complete search history.

(56) References Cited

U.S. PATENT DOCUMENTS

| | | |
|---|---|---|
| 4,333,263 A | 6/1982 | Adey |
| 4,966,096 A | 10/1990 | Adey |
| 5,097,795 A | 3/1992 | Adey |
| 5,527,456 A | 6/1996 | Jensen |
| 5,573,669 A | 11/1996 | Jensen |
| 5,715,774 A | 2/1998 | Adey et al. |
| 5,778,823 A | 7/1998 | Adey et al. |
| 5,851,398 A | 12/1998 | Adey |
| 6,572,770 B1 | 6/2003 | Stewart, III et al. |
| 2009/0139927 A1 * | 6/2009 | Kania et al. .................. 210/602 |

FOREIGN PATENT DOCUMENTS

| | | | |
|---|---|---|---|
| DE | 10322111 A1 | | 12/2004 |
| GB | 2453194 A | | 4/2009 |
| JP | 06-178626 A | * | 6/1994 |
| JP | 09-141280 A | * | 6/1997 |
| JP | 20000209971 A | | 8/2000 |
| JP | 2006-129756 A | * | 5/2006 |
| JP | 2007295879 A | | 11/2007 |
| WO | 2005082129 A1 | | 9/2005 |

OTHER PUBLICATIONS

Database WPI, "XP002663618", Week 200510, Thomson Scientific, London, GB, AN 2005-084358 & JP 2005 013201 A (Niiya H), Jan. 20, 2005, abstract.
Adey, et al, "Phosphorus Removal from Natural Waters Using Controlled Algal Production", Restoration Ecology, Mar. 1993, pp. 29-39.

* cited by examiner

*Primary Examiner* — Fred Prince
(74) *Attorney, Agent, or Firm* — John Wilson Jones; Jones & Smith, LLP (57) ABSTRACT

A three-dimensional grid for use as an algal turf growing surface contains a horizontal planar basal net containing a series of horizontal planar members and upwardly directed members.

23 Claims, 5 Drawing Sheets

BASAL SCREEN FOR ENHANCING ALGAL BIOMASS GROWTH

This application claims the benefit of U.S. patent application Ser. No. 61/246,477 filed on Sep. 28, 2009, herein incorporated by reference.

FIELD OF THE INVENTION

The invention relates to basal screens useful for removing nutrients and/or waste from water and for enhancing or producing biomass in systems containing algal communities, including algal turf scrubbing systems, and has particular applicability when filamentous diatoms are components of the algal community.

BACKGROUND OF THE INVENTION

Cultured complex communities of attached algae, sometimes referred to as algal turf systems, have been used to manage water quality and to scrub a variety of nutrients or contaminants from marine, estuarine, and fresh water. In particular, such algal communities do not demonstrate the sensitivity and instability characteristics of monocultures of algae, and thus are useful in the removal of nutrients, such as phosphorus, and pollutants from wastewater. U.S. Pat. No. 4,333,263 describes the use of algal turf systems containing attached algae communities to primarily metabolically remove carbon dioxide, nutrients and other pollutants from wastewaters; U.S. Pat. Nos. 4,966,096 and 5,097,795 describe equipment for carrying out this function; and U.S. Pat. No. 5,851,398 describes a method for removing pollutants with algal turf scrubbing systems by precipitation of the pollutants onto and/or into the cells or cell walls of an algal turf growing in a flowing column of water, all of said patents are hereby incorporated by reference in their entirety. Algal turf systems are also known to increase or enhance the production of algal biomass. Algal turf systems containing cultured communities of attached algae have also been described in U.S. Pat. Nos. 5,527,456; 5,573,669; 5,715,774; 5,778,823; 5,851,398; and 6,572,770, all of which are herein incorporated by reference.

When scaled-up, algal turf systems may be used to restore impaired rivers, bays and lakes. For instance, algal turf systems have been successfully scaled-up for nutrient removal from point-source, nonpoint source and open surface waters. In addition to its successful use in the removal of nutrients (such as nitrogen, phosphorus and carbon dioxide) and other contaminants, the literature also illustrates the successful use of algal turf systems, such as the commercial Algal Turf Scrubber® (ATS), for the injection of oxygen into a wide variety of waters. For instance, in Adey et al., "Phosphorus Removal from Natural Waters Using Controlled Algal Production," pp. 29-39, Restoration Ecology (March 1993), the author discusses the use of ATS to scrub the nutrient phosphorus from agricultural wastewaters. This article, and the above-identified patents, discloses the role of algal turf to remove phosphorus both through (1) metabolic uptake and (2) the physical removal of phosphorus attached to organic particulates. In these references, particulate trapping, i.e., physical removal, is accomplished within the web of algal filaments enhanced by the mucilage production of blue-green algae and diatoms.

Algal turf systems are often characterized by a basal component of algal filaments self-attached to a screen, such as a plastic screen. The screen functions as a growing surface for the algal turf. An epiphytic community of filaments and cells are attached to the basal filaments and bulked-up with the trapping of mostly algal unicells by the built up meshwork of algae. Typically the basal filaments are green algae, such as *Cladophora* and *Rhizoclonium* in fresh water; red algae, such as *Polysiphonia* and *Herposiphonia*; and brown algae, such as *Ectocarpus* and *Giffordia* in both estuarine and sea waters.

In previous floways using algal turf systems, filamentous green algae have been principally used to produce considerable algal communities or algal biomass. In particular, when accompanied by extensive natural energies, such as currents or wave oscillations, the algal biomass have sustained significant levels of productivity. In some cases the algal biomass has been used as an animal feed and fertilizer. The use of algal turf systems have also been expanded to aquaculture, the treatment of tertiary sewage system, and agricultural canal amelioration of nutrients. In addition, algal turf systems have been successfully used in the production of commercial quantities of fish, such as *Tilapia*.

Under some water treatment conditions, filamentous diatoms become the primary basal support filaments in algal turf systems. This is the case in those situations where the water being treated lacks natural periphyton and is heavily dominated by filamentous diatoms. In such cases, the filamentous diatoms overwhelm the green and red basal filaments. In green, red or brown filamentous algae, in which the cell walls of adjacent cells are an integrated structure, the filaments have considerable tensile and shear strength. These filaments are able to withstand the flow and surge of water on an algal turf floway during the entire 7-21 day typical harvest cycle even when heavily encrusted with epiphyles. Slough or filamentous breakage and loss only become serious at the end of the harvest cycle which is seasonally determined. In the short term, individual cells of green, red or brown filamentous algae can die without compromising the integrity of the green filament.

Unlike green, red and brown algal filaments whose often massive cellulosic wall is continuous from cell to cell with no break, diatom filaments have an entirely different structure. Filamentous diatoms have their cells attached to each other by much weaker mucous links or thin silica threads. When filamentous diatoms dominate the algal turf basal filaments, frequent breakage and random slough occurs resulting in turf loss before the end of the harvest cycle.

Some filament loss may also be attributable to the substrate used to date in algal turf systems. The traditional substrate in an algal turf system, such as an ATS, is a 2-dimensional plastic screen. Several varieties of plastic screen have been employed including extruded high density polyethylene (HDPE) of 3×5 mm mesh, and woven multifilament nylon and nylon/HDPDE mesh. The dominant diatom communities that occur on some river algal turf systems quickly attach to the 2-dimensional plastic screens but their filaments constantly "shear-off" in the moderate energy environment of an algal turf system, producing a lower standing crop and ultimately lower water remediation capabilities and by-product biomass.

The filament loss exhibited from diatoms limits efficiency during harvesting of the algal turf. Typically, harvesting is effectuated by scraping or vacuuming directly on the drained screen following full biomass buildup. Further, the presence of diatoms negatively affects the productivity of those sloughed filaments and cells. In situations where diatom filaments form the primary structure of the algal turf, estimated filament loss to slough is as high as 50%. While some of this loss may be captured in slough mesh bags or removed by centrifugation, these processes result in increased operations and maintenance costs. In addition, sloughed algal biomass may be captured via outflow filtration systems; however this method results in loss of system productivity. Overall, the lesser shear strength of diatom filaments in the moderate energy environment of the algal turf system increased slough rate, reduced expected productivity by 25-50% and reduced nutrient removal by 10-30%.

Improvements in the use of algal turf systems, especially when used with diatom filaments, are therefore needed to increase harvesting and productivity of water treatments where primary basal support filaments are filamentous diatoms.

SUMMARY OF THE INVENTION

Efficiency and productivity of treated water may be improved by use of a three-dimensional basal screen. The three-dimensional basal screen is especially useful as an algal turf growing surface for filamentous algae including filamentous diatoms.

The basal grid may contain a horizontal planar net or screen which is composed of a series of horizontal planar members which form a multitude of open-spaced grids. Upwardly directed members extend vertically from the horizontal planar members. The upwardly directed members may be a single filament or may consist of a bundle of filaments.

The basal screen may be composed of fiberglass, plastic, natural fibers, metallic substrates, polyester, organic fibers or woven filaments.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

The basal screen used for the growing surface herein is three-dimensional. When used in an algal turf system, the three-dimensional screen described herein provides greater structural strength, including tensile strength and shear strength, over the screens previously seen in the art. In addition, the basal screens described herein provide greater surface area for attachment of the algal turf over the two-dimensional screen grids previously seen in the art.

The three-dimensional basal screens described herein are highly useful in the development of an algal community. The algal community referenced herein may contain filamentous and non-filamentous algae. The 3-D effect improves the productivity seen in 2-D screens, especially when the algal community is principally composed of diatoms, including filamentous diatoms, though desirable effects are also observed when using the screens for dominant species other than diatoms.

Figure 1:
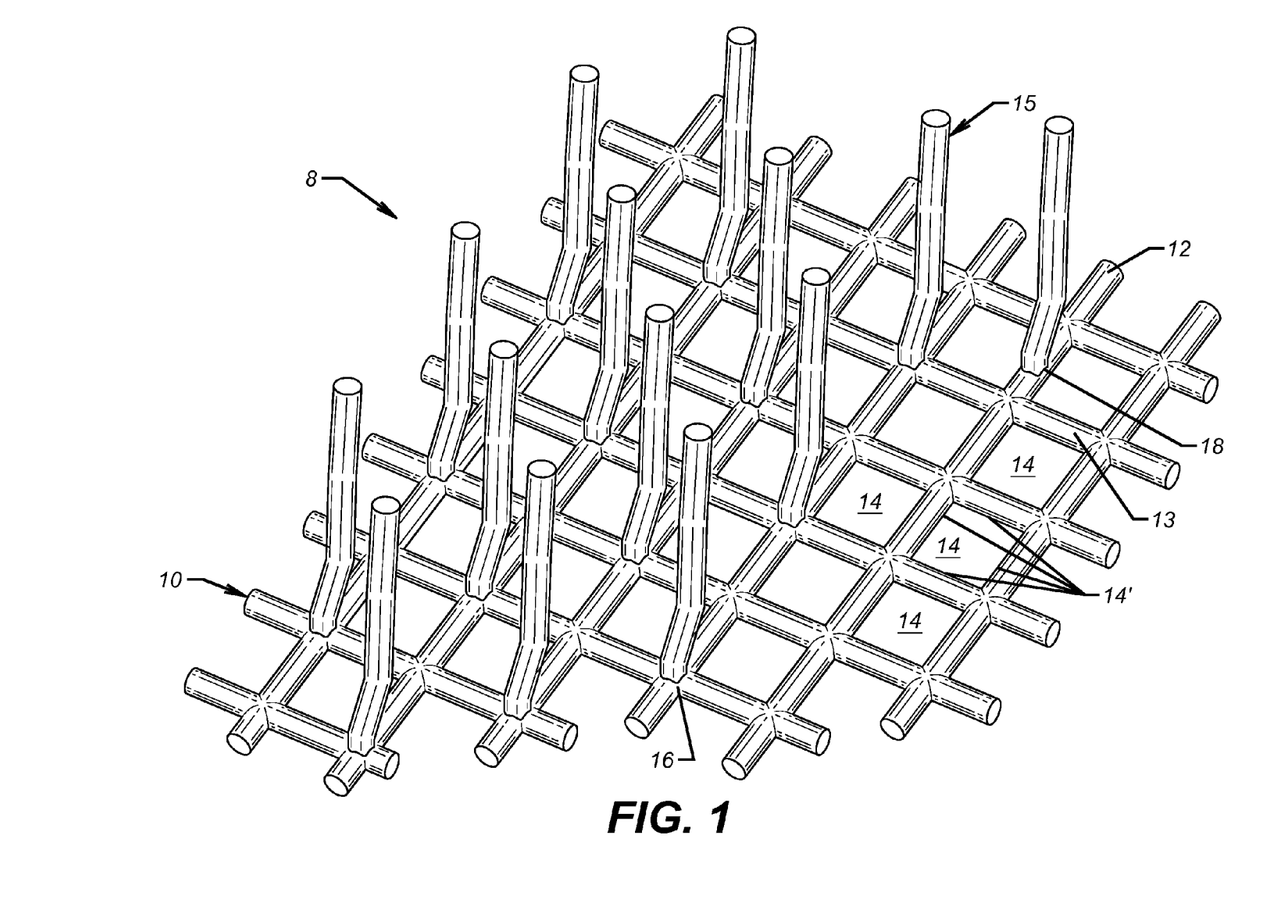
FIG. 1 depicts a basal screen described herein containing upwardly directed filaments for providing an increased growing surface for algal turf.

Referring to FIG. 1, the basal screen 8 consists of a horizontal planar basal net or basal screen 10. (The use of the term "basal net" herein shall refer to a net as well as a screen.) Basal net 10 is composed of a series of horizontal planar members 12 and 13. In a preferred embodiment, horizontal planar members 12 and 13 form a multitude of adjoining open-spaced grids, 14'. The open areas 14 defined by open-spaced grids 14' prevent anaerobic conditions and allow full circulation of water through the floway.

As shown, horizontal planar members 12 and 13 intersect with each other at 90°, though horizontal members 12 and 13 may be in other horizontal planar spatial designs provided they form a two-dimensional basal net upon which an algal turf may attach.

In addition to horizontal planar members 12 and 13, basal screen 8 further contains upwardly directed members 15 which, when subjected to floway conditions, typically extend in a non-horizontal direction from horizontal planar members 12 and 13 of horizontal planar basal net 10. Placement of upwardly directed members 15 onto horizontal planar basal net 10 may be designed in any manner which increases the surface area of basal screen 8 when it is exposed to incoming water during floway conditions. In a preferred embodiment, the upwardly directed members are vertical though the upwardly directed filaments may be positioned at any angle from horizontal planar members 12 and 13. In one embodiment, the upwardly directed members are perpendicular to horizontal planar basal net 10.

Upwardly directed members 15 may be extended from any place on horizontal planar basal net 10 including nodes 16 (where horizontal planar member 12 intersects with planar member 13) or along the length of horizontal planar member 12 and/or 13 (shown in FIG. 1 as 18). Typically, upwardly directed members 15 are attached at one or more nodes 16.

Figure 2:
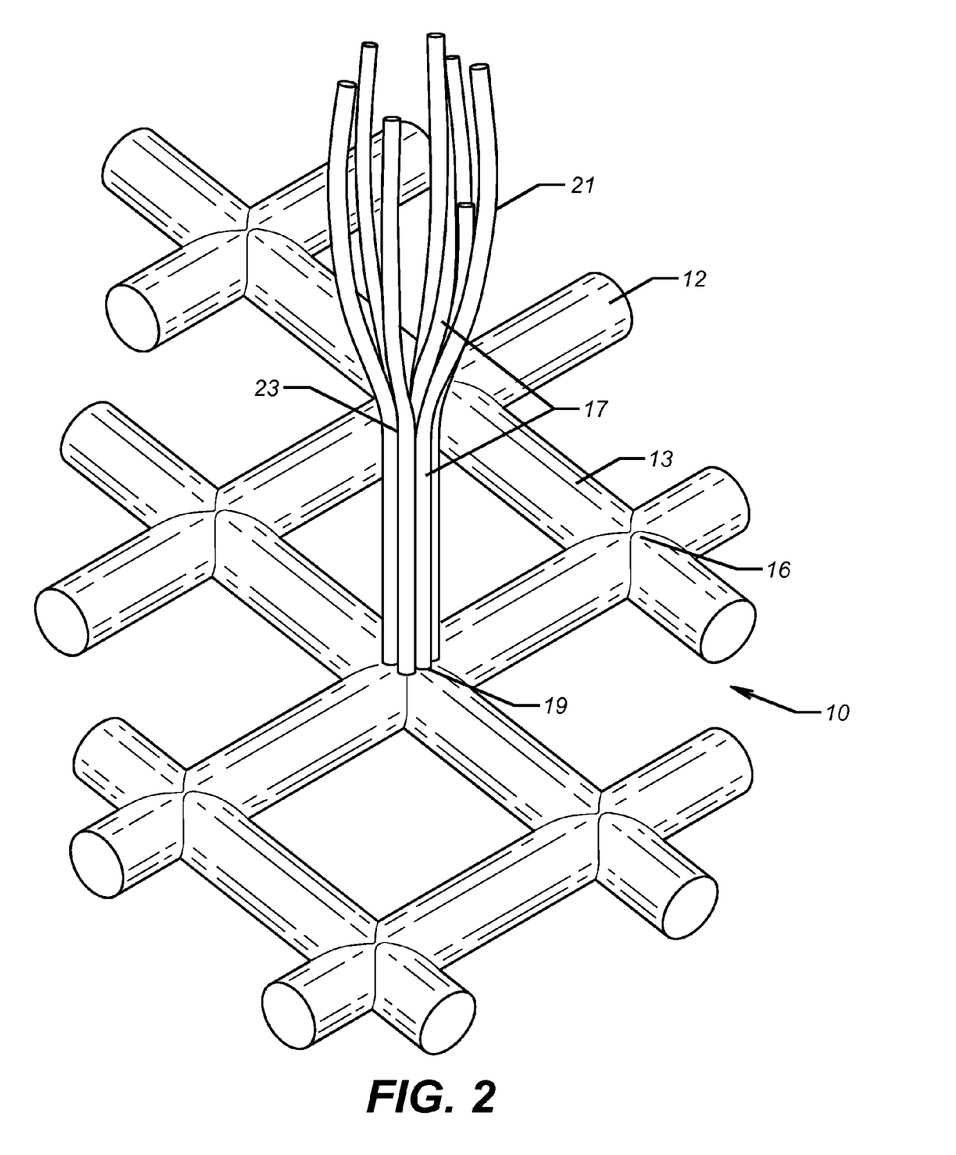
FIG. 2 illustrates a single vertical filament design for the upwardly directed filaments.

The upwardly directed filaments 15 may individually or collectively be a single filament (monofilament) or may consist of filaments grouped or bundled together (multifilament) or any other configuration of designed shaped filaments. FIG. 1 illustrates one design of upwardly directed members 15 as single filament. In FIG. 2, a multitude of upwardly directed filaments 17 is bundled together and extend from horizontal planar basal net 10. While FIG. 2 shows placement of the upwardly directed members 17 at node 19, one or more upwardly directed members may extend from any place along the length of either the horizontal planar member 12 and/or horizontal planar member 13. The upwardly directed filaments shown in FIG. 2 have multiple upper crests 21 which extend upwardly from stalk 23 of the upwardly directed filaments. As shown, the base or lower half of the filament bundles are secured together at the bottom of stalk 23 while the upper portion or upper crest 21 of the filaments are unsecured from each other. During operating conditions, the upwardly directed members are pushed upward from the force of the water and/or flow in the direction of the inflow treatment water stream.

In another embodiment, horizontal planar member(s) 12, horizontal planar member(s) 13 and/or upwardly directed member(s) 15 may be composed of a multitude of filaments, such as filaments which are helically wound with each other. Horizontal planar basal net 10 may also contain a number of different shapes and designs of upwardly directed members including open loops, twisted filaments and twisted loops. Any of a number of designs for the upwardly directed members may be used which provide increased surface area, the requisite rigidity to prevent dislodgment from the grid as well as flexibility for attachment of the algal turf.

The basal net is preferably sized to maximize the effect of the upwardly directed members. Optimization of the dimensions of the planar basal net 10 and open-spaced grids 14 are dependent on the locality being treated, the type of water being treated, the size of the floway and the incoming flow rate of the treated water. In a preferred embodiment, open-spaced grids 14 of planar basal net 10 are of a dimension such that channels are unable to form between upwardly directed members 15 attached to horizontal planar members 12 and 13. Since channels serve as conduits through which inflowing water passes, open-spaced grids 14 are dimensioned such that the filamentous diatoms may attach onto the upwardly directed members as well as the horizontal planar members. In addition, open-spaced grids defining horizontal planar basal net 10 are dimensioned such that upwardly directed members 15 do not allow inter-filament sluicing. Preferably, the open-spaced grids are square-shaped measuring between from about 0.5 to about 2 cm. The upwardly directed members are typically between from about 1 cm to about 5 cm in height. The spacing between upwardly directed members 15 should be preferably less than about 5 cm and more typically less than 3 cm. Typically, if the height of upwardly directed members 15 is less than 5 mm or the distance between upwardly directed members 15 is less than 5 mm or exceeds 5 cm, productivity will be decreased.

Figure 3A:
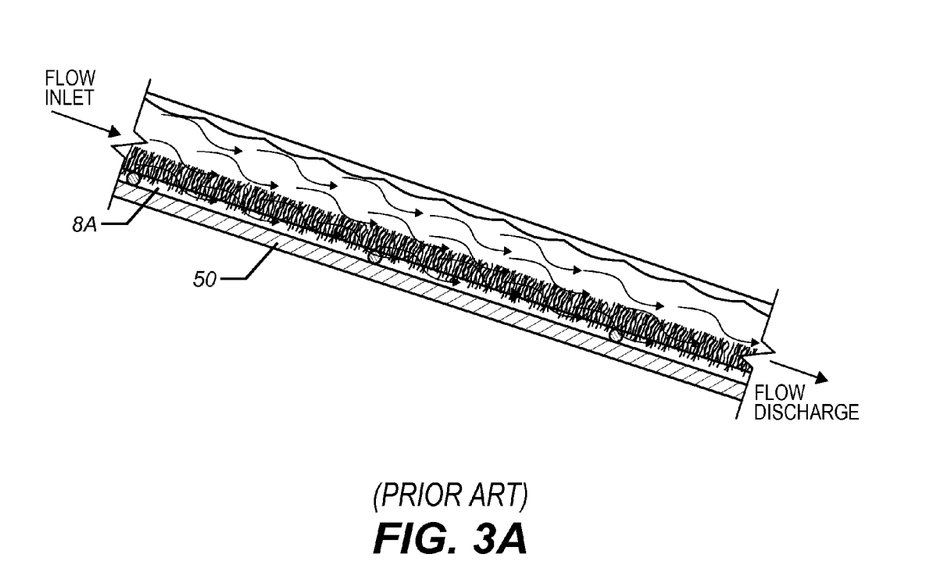
FIGS. 3A and 3B illustrate a floway using a two-dimensional screen grid of the prior art.
Figure 3B:
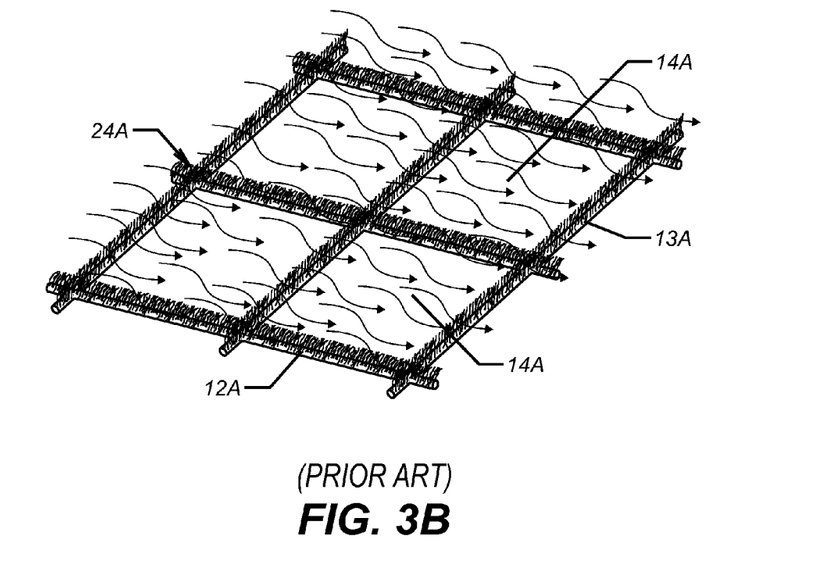
Figure 4A:
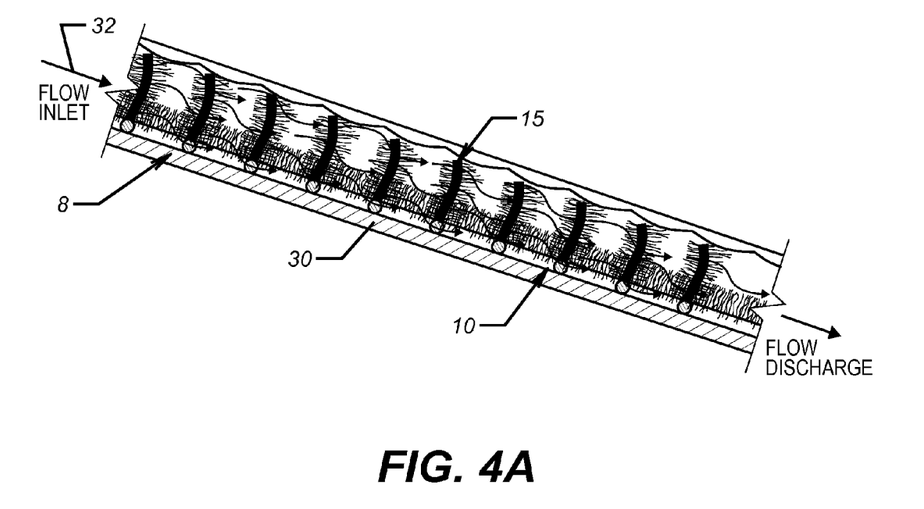
FIGS. 4A and 4B illustrate a floway using an exemplary three-dimensional basal screen of the invention.
Figure 4B:
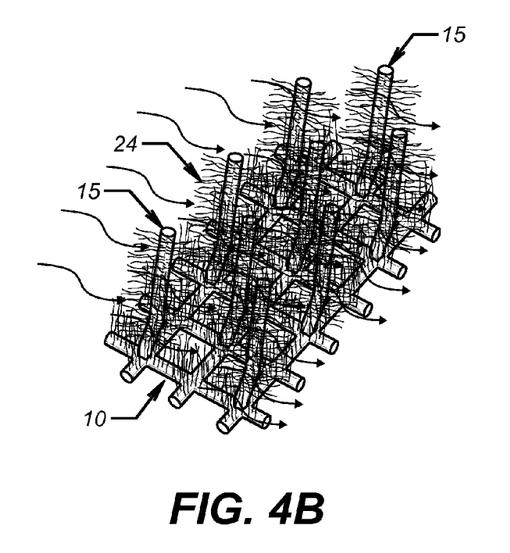

FIGS. 4A and 4B illustrate an embodiment of the invention described herein. FIG. 4A depicts a floway using a three-dimensional screen grid 8 of brush conformation wherein screen grid 8 is placed into floway receptacle 30. Screen grid is composed of horizontal planar basal net 10 which is defined by the intersecting horizontal planar members. Treatment water through flow inlet 32 passes through upwardly directed members 15. FIGS. 3A and 3B illustrate operation of a prior art screen. In FIG. 3A, floway 50 contains a two-dimensional screen grid 8A which is composed of two horizontal planar members 12A and 13A. The horizontal planar members define the open-spaced grid. Open area 14A of the open-spaced grid(s) allows for circulation of inflow water through floway 50. Screen grid 8A renders floway 50 less efficient for production of algae 24A than floway 30 containing basal screen 8. In fact, in most instances, the presence of upwardly directed members 15 attached to horizontal planar basal net 10 in screen grid 8 entraps filamentous algae and/or diatoms 24 at a level of at least double productivity of that of the prior art grid design 50. The effect of entrapment of algae by the three-dimensional grid is illustrated in FIG. 4B which represents an exploded section of treatment water through the floway of FIG. 4A. Entrapment in a two-dimensional grid is confined to the horizontal plane of the grid, defined by horizontal planar members 12A and 13A, as much of the water flow surges above the grid, as illustrated in FIG. 3B. The conformation of the screen grid of FIGS. 3A, 3B, 4A and 4B may further be open cell foam or a three dimensional fibrous mat or any other conformation that provides the increased surface for attachment of algal turf.

Ultimately the method of harvesting filamentous diatoms will also be a factor in designing the 3-D grid design described herein. Harvesting of algal biomass from the algal turf substrate include such conventional techniques harvesting by scraping algae off the growth substrate, utilization of vacuum (either by hand or mechanical equipment), reel-off harvest methods, wheeled harvesters disposed to roll along the curbs of the floway and angled plowing systems on conical floways. In a preferred embodiment, the algal biomass is harvested by wet or dry vacuuming, wheeled harvesters and a combination. In some instances, it may be desired to use a porous fabric backing on the bottom surface of the screen in order to increase the structural strength of the basal screen nets when various harvest methods are employed.

The components of screen 8 (horizontal planar members and upwardly directed members) may be monofilaments or multi-filaments or combination of the two. The monofilaments and multi-filaments defined herein may be of any configuration or composed of any material.

Preferably, the horizontal planar members and/or upwardly directed members comprising the components of screen 8 are composed of fiberglass, plastic, organic fibers, natural fibers (including wood, treated cotton, treated hemp, etc) or are metallic (such as metallic fibers or ceramics). The conformation of the components may be varied and may include straight, twisted, woven or braided filaments. Preferably, the material used to make the basal screen exhibits a specific gravity sufficient to prevent the screen grid from being dislodged from the floway and to prevent significant circulation reduction. Most preferably, the material used to make the basal screen has a specific gravity greater than that of water. The upwardly directed members may be constructed of low specific gravity to induce flotation in the water column. In addition, since the grid is exposed to long periods of sunlight, it is preferred that the screen be composed of materials which are resistant to UV light.

The basal screen defined herein may be prepared by hand weaving filamentous fibers or by machine weaving. The upwardly directed members may extend from the horizontal planar basal net in a hooked or tied fashion. Further, the grid may be prepared, such as where the screen is made of plastic, by extrusion. In addition to weaving, the grid may be prepared by other conventional manufacturing methods such as by tying, gluing or welding the components. The upwardly directed members and the horizontal planar members may be a uniform filament provided that the upwardly directed filaments are not within the same horizontal plane as the horizontal planar members. For instance, the basal screen may be prepared by a weaving process wherein some or all of the components of the basal screen are composed of a uniform woven filament wherein the upwardly directed portion of the uniform filament is not within the same horizontal plane as the horizontal planar members of the uniform filament.

Preparation of the basal screen is preferably tailored to maximize the surface area of the screen to which algae will be exposed. While the upwardly directed members and the volume created by the upwardly directed members provide greater surface area, the compounding of multiple microsurfaces on the horizontal planar members may further provide the desired result of increased surface area.

The horizontal planar members and/or upwardly directed filaments may be translucent or transparent in order to reduce shading and increase productivity.

The basal screens described herein offer a superior media for the growth of algae including diatoms as well as filamentous algae and filamentous diatoms. Such improvement in productivity is apparent during all seasons of the year. In particular, the three-dimensional basal screen described herein exhibits increased production in winter conditions (even at water temperatures below 40° F.) when the attached biomass may be low as well as in summer conditions when biomass levels are high. Mean summer productivity using the three-dimensional basal screens has exceeded 40 g/m$^2$/day. Further, mean productivity peak temperatures and one half light peak have seen over 50 g/m$^2$/day, greater than three times than when two-dimensional basal screens have been used.

Further, the three-dimensional basal screen described herein is effective with a very broad spectrum of algae, including green algae and brown algae. The basal screens described further are particularly useful with filamentous diatoms. Unlike green algal filaments (or red or brown algal filaments in sea water), filamentous diatoms are basically fragile and subject to breakage in the energy-rich algal turf environment. Unlike the screen grids of the prior art where filamentous diatoms that attached to the screen became entangled in the canopy of the dominant filamentous green algae remaining on the floway, the grid described herein efficiently retains the filamentous diatoms on the algal turf floway.

The 3-D algal turf solves the diatom sloughing problem in two principal ways. First, the upwardly directed filaments provide an additional surface for attachment of filamentous diatoms. As a result, considerable additional biomass may be supported at shorter individual filament lengths. Second, in addition to increasing surface area to provide additional attachment sites for filamentous diatoms, the cubic space provided by the upwardly directed filaments modifies the extremely important vertical and lateral surging or elliptical wave motion to a small cell swirling motion that provides equal mixing with less tensile stress to the algal filaments.

While the screen grid described herein offers a superior media for the growth of filamentous diatoms, it further provides a superior surface for the growth of green and red algae and provides an improvement over previously used grid surfaces. A principal advantage of the screen grid described herein is its ability to overcome the slough (or algal loss) which results from insufficient filamentous green, red or brown algae to develop. In addition, it provides the requisite support for the algal turf community to reach maturity seen in the prior art devices.

The present invention more than doubles algal productivity and produces an entirely new field of potential process improvement. Additionally, it achieves substantially greater removal of pollutants, including removal of both nutrients such as phosphorus and heavy metals, from wastewaters. Still further, the screen grid described herein provides efficient production of nutrient-laden biomasses for use as a source of animal feed, energy, fertilizer or for other uses.

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

EXAMPLES

Example 1

A 3-D screen grid was hand woven from 1-2 cm long Dacron fibers. The Dacron fibers were selected since they provided for minimal degradation under solar UV. The performance of the 3-D screen was compared with 2-dimensional grids which were composed of off-the-shelf, deep pile throw rugs. The grids were used in an ATS system on the Chesapeake's Great Wicomico River (a 10-14 ppt saline environment at about mid-Bay, north to south). While some of the 2-dimensional rugs had a structure that considerably enhanced diatom retention, after several months, the woven Dacron 3-dimensional (3-D) test screens provided the greatest productivity of all the test screens especially in the central part of the ATS test floway.

Example 2

Figure 5:
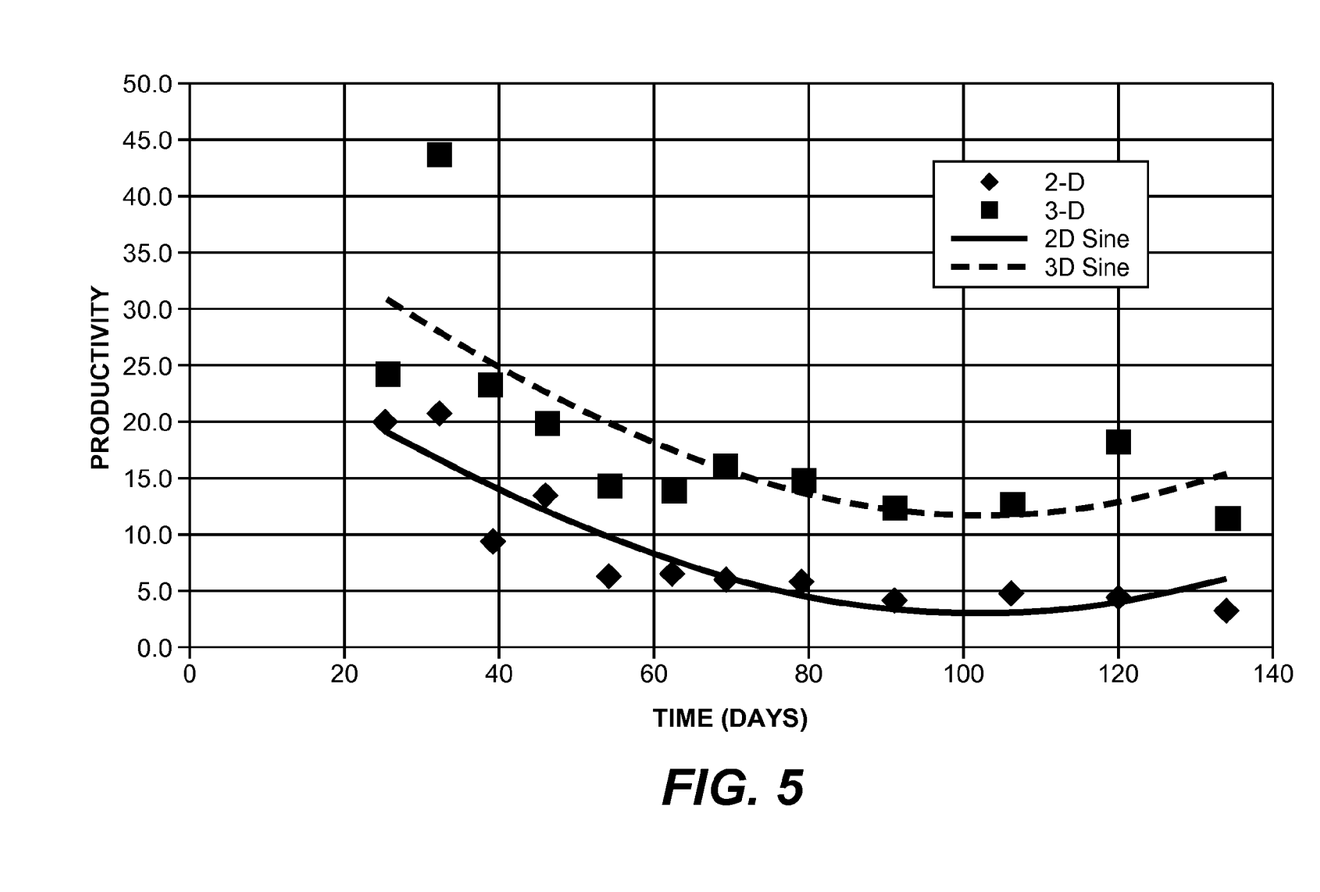
FIG. 5 contrasts productivity using an illustrative three-dimensional basal screen of the invention and a 2-dimensional screen grid of the prior art.

3-D screens, arrayed with standard 2-D algal turf screens both above and below, were compared to 2-D algal turf screens. The results in productivity are illustrated in FIG. 5 where the plotted points are means of two 3-D and three 2-D screens and demonstrate that the 3-D screens exhibit over 2 times the productivity of the standard 2-D screens. A t-test demonstrated a high level of significance, p=0.0003. The mean production for the 3-D screen during the test period was 11.5 g/m$^2$/day, compared to 4.0 g/m$^2$/day for the 2-D screens.

The foregoing disclosure and description of the invention is illustrative and explanatory thereof, and various changes in the size, shape, and materials, as well as in the details of illustrative construction and assembly, may be made without departing from the spirit of the invention.

What is claimed is:

1. A three-dimensional basal screen for growing algae comprising:
    (a) horizontal planar members joined together at nodes to form adjoining open-spaced grids; and
    (b) upwardly directed members extending from at least some of the horizontal planar members
wherein at least one of the following conditions prevails:
    (i) at least some of the horizontal planar members and/or upwardly directed members are independently selected from monofilaments and multi-filaments;
    (ii) the horizontal planar members, upwardly directed members or both horizontal planar members and upwardly directed members are composed of fiberglass or natural fibers;
    (iii) at least some of the horizontal planar members or upwardly directed members are straight filaments, twisted filaments, woven filaments or braided filaments;
    (iv) at least some of the upwardly directed members are helically wound filaments; or
    (v) the horizontal planar members and upwardly directed members are a uniform filament wherein the upwardly directed portion of the uniform filament is in a different plane than the horizontal planar members.

2. The three-dimensional basal screen of claim 1, wherein the horizontal planar members are perpendicular to each other.

3. The three-dimensional basal screen of claim 1, wherein at least some of the upwardly directed members extend from the basal screen at the nodes.

4. The three-dimensional basal screen of claim 1, wherein at least some of the horizontal planar members and/or upwardly directed members are independently selected from monofilaments and multi-filaments.

5. The three-dimensional basal screen of claim 1, wherein the open-spaced grids are square-shaped, each side measuring between from about 0.5 to about 2 cm.

6. The three-dimensional basal screen of claim 1, wherein the horizontal planar members, upwardly directed members or both horizontal planar members and upwardly directed members are composed of fiberglass or natural fibers.

7. The three-dimensional basal screen of claim 1, wherein at least some of the horizontal planar members or upwardly directed members are straight filaments, twisted filaments, woven filaments or braided filaments.

8. The three-dimensional basal screen of claim 1, wherein at least some of the upwardly directed members are helically wound filaments.

9. The three-dimensional basal screen of claim 1, wherein the horizontal planar members and upwardly directed members are a uniform filament wherein the upwardly directed portion of the uniform filament is in a different plane than the horizontal planar members.

10. A method of removing nutrients and/or waste from water and producing an algal biomass comprising the steps of:
   (a) providing a growing surface for an algal biomass, the growing surface comprising a three-dimensional basal screen comprising horizontal planar members joined together at nodes to form adjoining open-spaced grids and upwardly directed members extending from at least some of the horizontal planar members;
   (b) exposing the three-dimensional basal screen to a flow of water and light and attaching algae onto the three-dimensional basal screen to form the algal biomass; and
   (c) harvesting at least a portion of the algal biomass from the three-dimensional basal screen.

11. The method of claim 10, wherein the horizontal planar members of the three-dimensional basal screen are perpendicular to each other.

12. The method of claim 10, wherein at least some of the upwardly directed members of the three-dimensional basal screen extend from either (a) a node or (b) from a horizontal planar member.

13. The method of claim 10, wherein the upwardly directed members of the three-dimensional basal screen consist of multi-filaments.

14. The method of claim 10, wherein the three-dimensional grid is an open cell foam or a three dimensional fibrous mat.

15. The method of claim 13, wherein the multi-filaments consist of helically wound filaments.

16. The method of claim 10, wherein the open-spaced grids are square-shaped, each side measuring between from about 0.5 to about 2 cm.

17. The method of claim 1, wherein the horizontal planar members and/or upwardly directed members are composed of plastic, fiberglass or woven filaments.

18. A method for purifying water of a waterway, comprising the steps of:
   (a) introducing into a receptacle a growing surface for algae, the growing surface comprising a three-dimensional basal screen comprising horizontal planar members joined together at nodes to form adjoining open-spaced grids and upwardly directed members extending from at least some of the horizontal planar members;
   (b) exposing the three-dimensional basal screen to a flow of water and light and thereby attaching algae onto the three-dimensional basal screen;
   (c) flowing the water from the waterway over the three-dimensional basal screen having the attached algae and promoting metabolic cellular-ambient water exchange between the algae and the waste and/or nutrients in the water; and
   (d) harvesting at least a portion of algae from the three-dimensional basal screen.

19. The method of claim 18, wherein the algae contains diatoms.

20. The method of claim 10, wherein the upwardly directed members extending from at least some of the horizontal planar members increase the surface area of the growing surface exposed to the flow of water and further wherein multiple micro-surfaces are compounded on the upwardly directed members further providing increased surface area.

21. A method of removing nutrients and/or waste from water comprising the steps of:
   (a) providing a growing surface for algae, the growing surface comprising a three-dimensional basal screen comprising a series of horizontal planar members which form a multitude of open-spaced grids and upwardly directed members extending from at least some of the horizontal planar members;
   (b) exposing the three-dimensional basal screen to a flow of water and light and attaching algae onto the three-dimensional basal screen, wherein the upwardly directed members of the growing surface increase the surface area of the growing surface exposed to the flow of water; and
   (c) harvesting at least a portion of the algae from the three-dimensional basal screen wherein the increased surface area of the growing surface further provides an increased surface for attachment of the algae.

22. The method of claim 21, wherein at least one of the following conditions prevail:
   (i) at least some of the horizontal planar members and/or upwardly directed members are independently selected from monofilaments and multi-filaments;
   (ii) the horizontal planar members, upwardly directed members or both horizontal planar members and upwardly directed members are composed of plastic, fiberglass, natural fibers or metallic substances;
   (iii) at least some of the horizontal planar members or upwardly directed members are straight filaments, twisted filaments, woven filaments or braided filaments;
   (iv) at least some of the upwardly directed members are helically wound filaments; or
   (v) the horizontal planar members and upwardly directed members are a uniform filament wherein the upwardly directed portion of the uniform filament is in a different plane than the horizontal planar members.

23. The method of claim 21, wherein multiple micro-surfaces are compounded on the upwardly directed members thereby providing increased surface area.

* * * * *